United States Patent [19]

Ando et al.

[11] 4,391,282
[45] Jul. 5, 1983

[54] COELIAC CAVITY ULTRASONIC DIAGNOSIS APPARATUS

[75] Inventors: Otaro Ando, Hino; Toshitaka Suwaki, Hachioji, both of Japan

[73] Assignee: Olympus Optical Company Limited, Tokyo, Japan

[21] Appl. No.: 198,246

[22] Filed: Oct. 17, 1980

[30] Foreign Application Priority Data

Oct. 24, 1979 [JP] Japan ............................. 54-136442
Oct. 24, 1979 [JP] Japan ............................. 54-136443
Sep. 12, 1980 [JP] Japan ............................. 55-126966

[51] Int. Cl.³ ............................................. A61B 5/02
[52] U.S. Cl. ........................................ 128/660; 128/4
[58] Field of Search ............................... 128/660–663, 128/4

[56] References Cited

U.S. PATENT DOCUMENTS 4,274,421 6/1981 Dory ................................. 128/660

FOREIGN PATENT DOCUMENTS 2950203 6/1980 Japan ................................. 128/660

OTHER PUBLICATIONS

Ikukoshi, Y., "Apparatus for Endoscopic and Ultrasonic Medical Diognosis", Japanese Pub. Unexamined Pat. Appln P. Sho-54/1984 1/9/79.

Hisanoga, K. et al., "A New Real-Time Sector Scanning System of Ultra-Wide Angle and Real-Time Recording", UTS in Medicine vol. 4, 1979.

Taylor, W. B. et al., "A High Resolution Transrectal Ultrasonographic System," UTS in Med. & Biol. vol. 5 No. 2, pp. 129–138 (1979).

*Primary Examiner*—Kyle L. Howell
*Assistant Examiner*—Francis J. Jaworski
*Attorney, Agent, or Firm*—Parkhurst & Oliff

[57] ABSTRACT

A coeliac cavity ultrasonic diagnosis apparatus which includes an ultrasonic transducer or scanner portion adapted to be inserted into a coeliac cavity to effect a sector scan of an ultrasonic beam to produce an ultrasonic image of internal tissues and in which the ultrasonic oscillator on the one hand and an ultrasonic reflecting mirror and rotary disc on the other hand are relatively rotated so as to effect the sector scan of the ultrasonic beam and the rotary angle of the rotary disc is detected so as to obtain a deflecting angle of the ultrasonic beam and a display on a cathode ray tube of a precise ultrasonic picture image.

22 Claims, 21 Drawing Figures

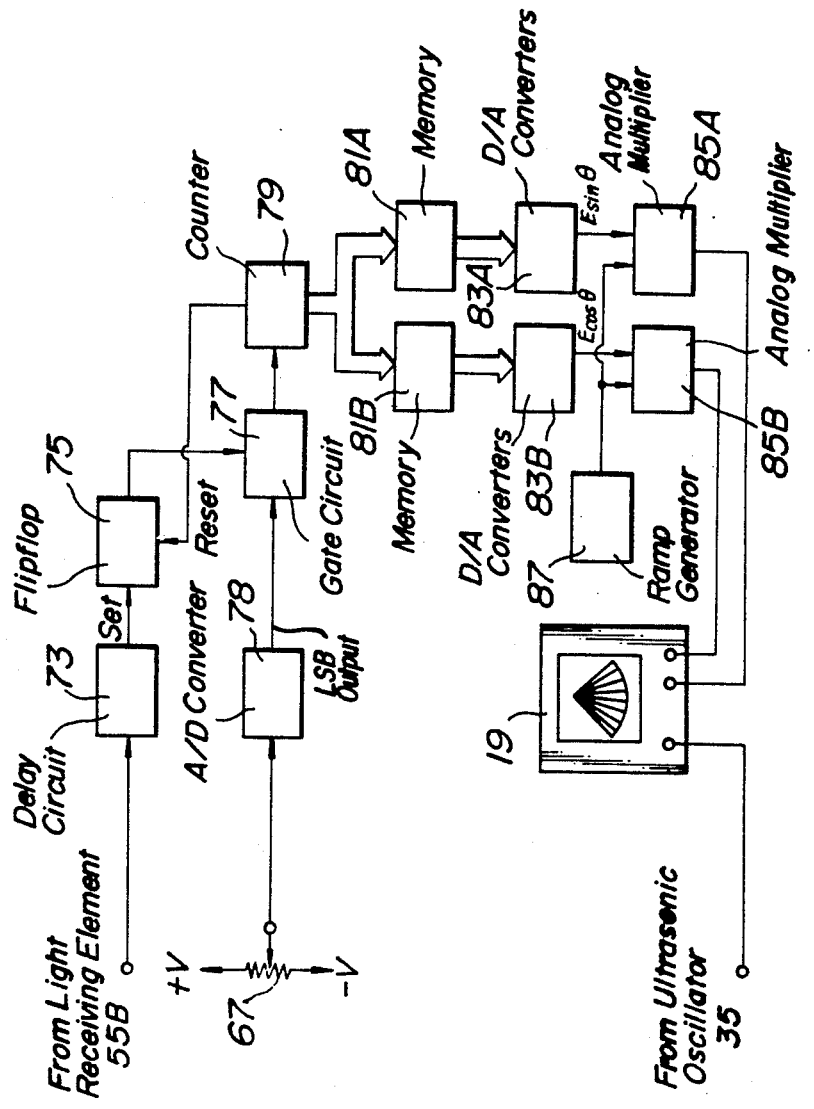

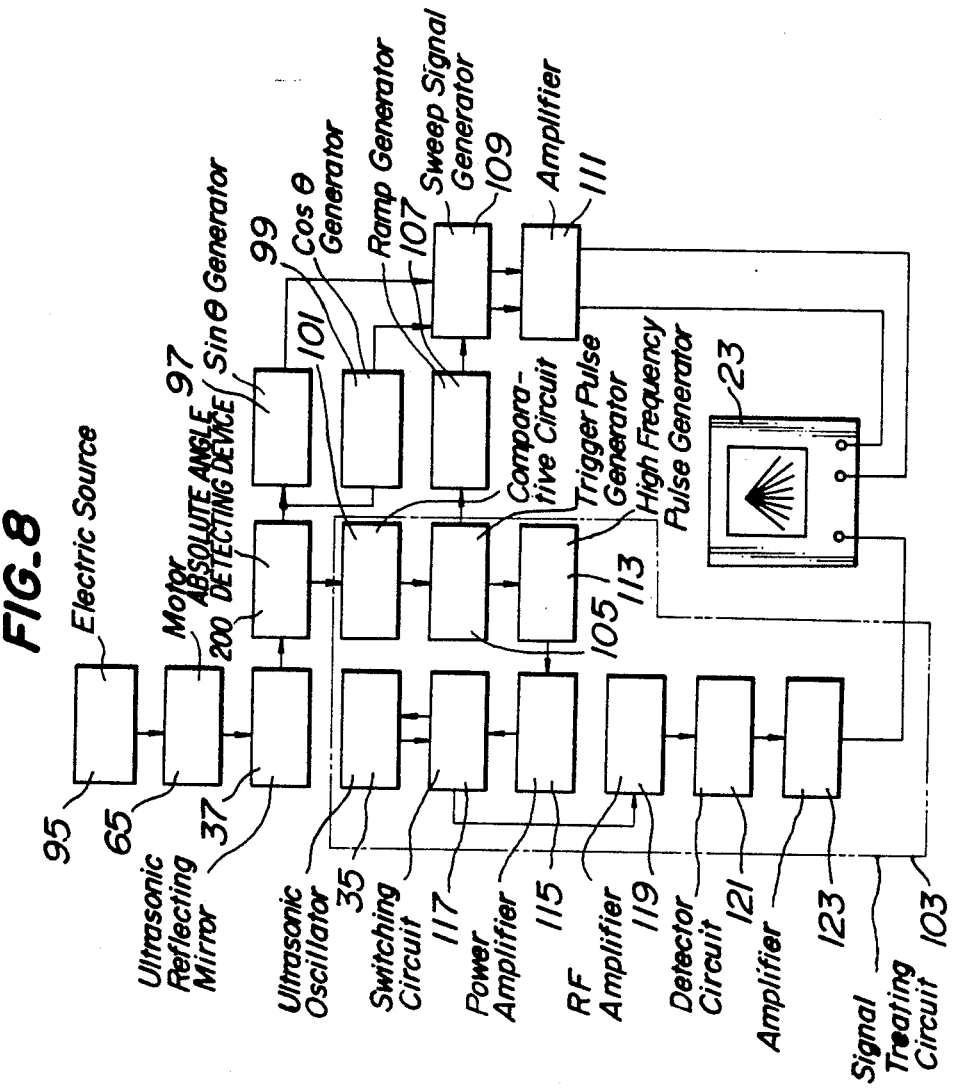

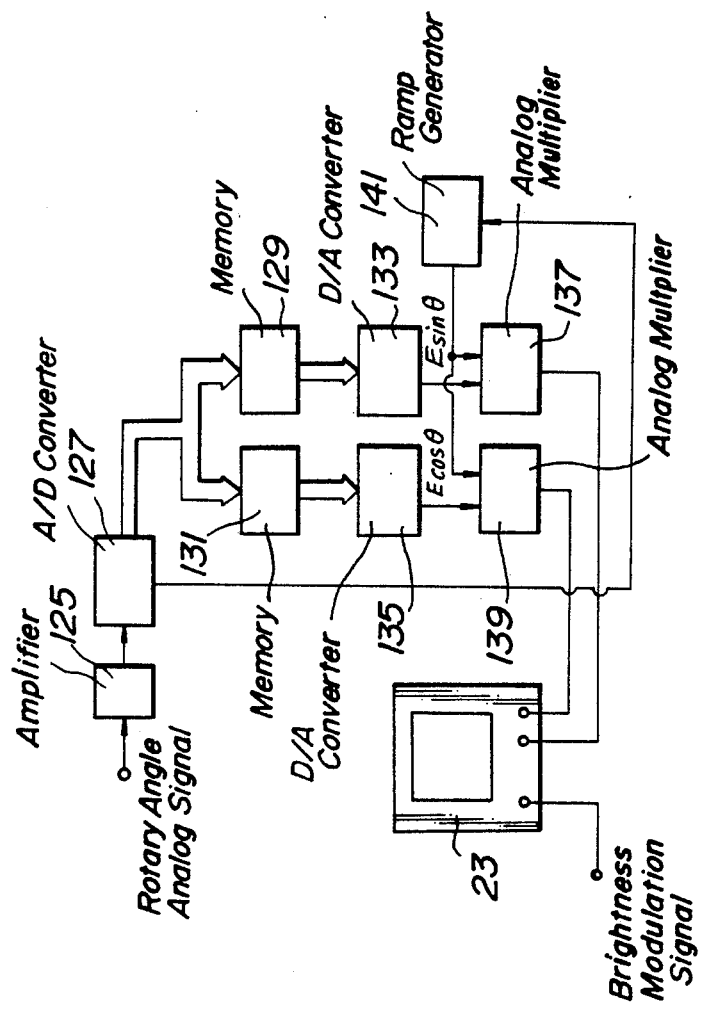

FIG_10A
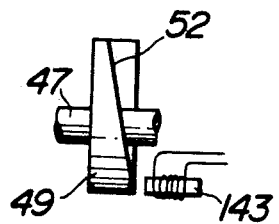
FIG_10B
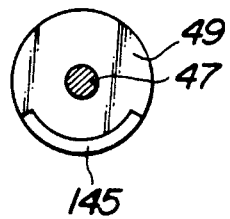

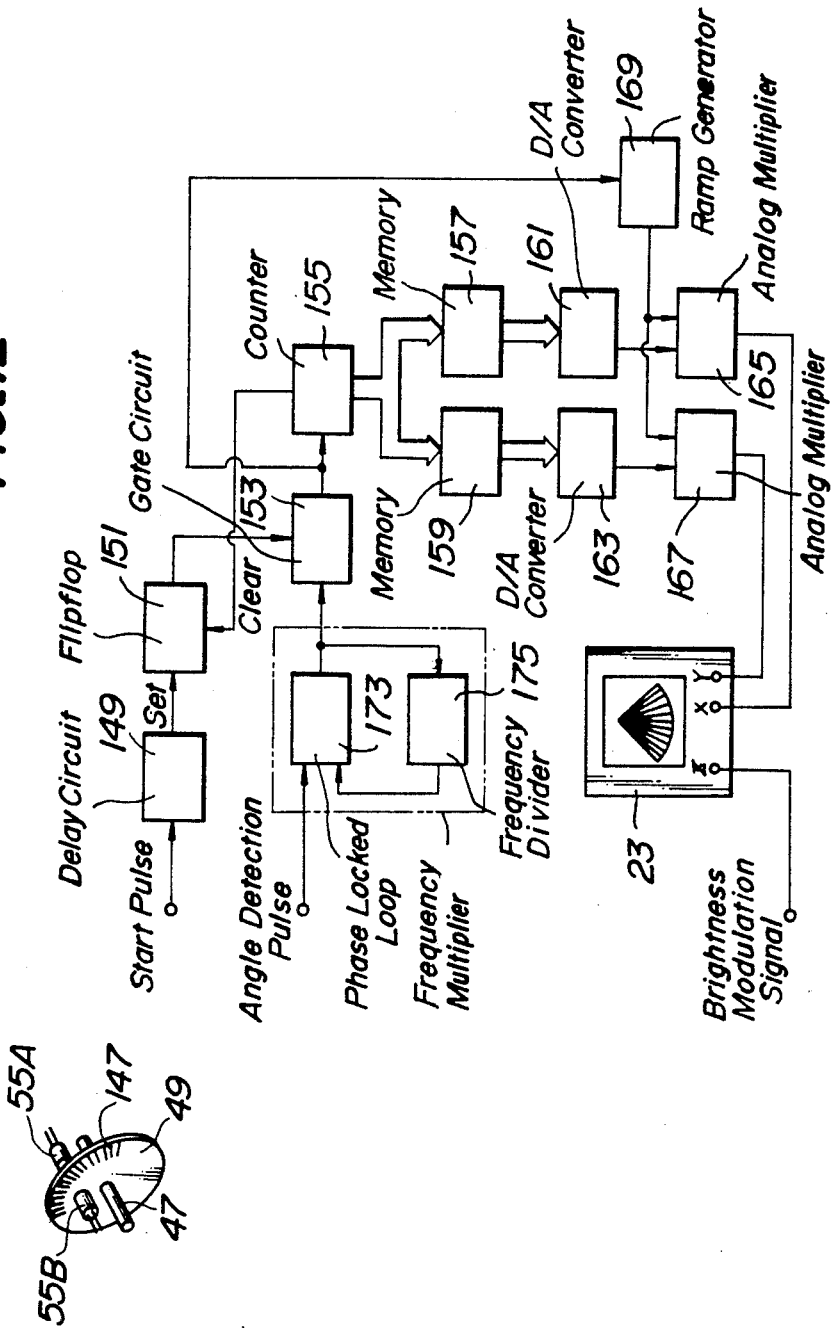

FIG.13A
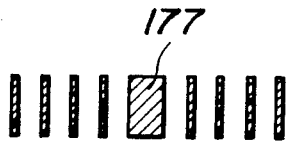
FIG.13B
FIG.14
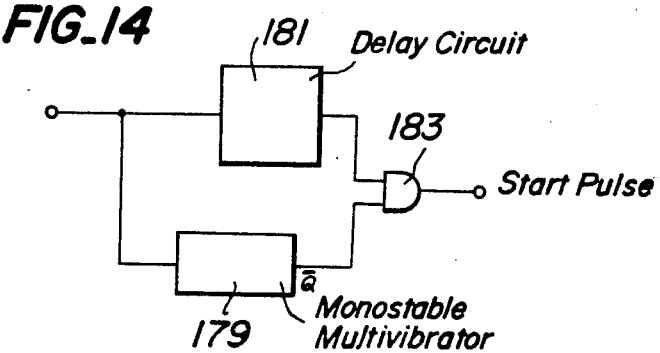
FIG.15A
FIG.15B
FIG.15C
FIG.16A
FIG.16B

COELIAC CAVITY ULTRASONIC DIAGNOSIS APPARATUS

BACKGROUND OF THE INVENTION

1. Field of the Invention

This invention relates to a coeliac cavity ultrasonic diagnosis apparatus which includes an ultrasonic oscillator that is, an ultrasonic signal transducer adapted to be inserted into a coeliac cavity to effect a sector scan of an ultrasonic beam to produce an ultrasonic image of internal tissues.

2. Description of the Prior Art

In clinics, usefulness of an ultrasonic diagnosis apparatus which makes use of an ultrasonic wave has recently been noted. An ultrasonic diagnosis apparatus which can emit an ultrasonic pulse into a physical body from the surface thereof, receive a reflected wave from various organs with the body and observe movement of the abdomen, heart and embryo in real time and a coeliac cavity ultrasonic diagnosis apparatus which includes an ultrasonic oscillator adapted to be inserted into the rectum, for example, so as to examine the prostate gland have both been used in practice.

The coeliac cavity ultrasonic diagnosis apparatus permits use at a location more closely spaced from an organ of a living body and an ultrasonic wave having a frequency which is higher than that used in the former apparatus which emits ultrasonic pulses into the physical body from the surface thereof. Accordingly, it has an advantage that it is possible to obtain a picture image having a high resolving power.

The conventional coeliac cavity ultrasonic diagnosis apparatus heretofore proposed includes an insertable portion which is rigid in construction. The rigid insertable portion can be inserted into a relatively shallow coeliac cavity such, for example, as the rectum which is simple in configuration so as to effect diagnosis of the prostate gland. But, it has recently been desired to develope apparatus which makes the best use of the coeliac cavity ultrasonic diagnosis apparatus, and which has a flexible insertable portion such that the ultrasonic oscillator can be inserted into a coeliac cavity which is complex in configuration and of a substantial depth such as the esophagus or the stomach and which can examine organs such as the heart, pancreas or the like under a high resolving power.

In such coeliac cavity ultrasonic diagnosis apparatus, in order to obtain a sector scan image, since the insertable portion is limited in diameter, the insertable portion is provided at its distal end portion with an ultrasonic beam scanning means including an ultrasonic oscillator, and the rear end portion of the insertable portion is connected to an operating portion which is provided with a driving means for the ultrasonic beam scanning means, and an angle detector for detecting the direction of the ultrasonic beam or the like.

In the above mentioned coeliac cavity ultrasonic diagnosis apparatus including a rigid insertable portion, the ultrasonic beam scanning means provided at the distal end portion of the insertable portion is connected through a rigid shaft to the driving means and an angle detector provided at the operating member. In this case, the direction of the ultrasonic beam corresponds to the rotation of the angle detector with a ratio of 1:1, so that use may effectivey be made of a sin, cos function generation type potentiometer which has heretofore been used as the angle detector.

But, when the insertable portion is flexible, the ultrasonic beam scanning means must be connected through a flexible power transmission member such, for example, as a coil wire to the driving means and angle detector. In this case, the direction detected by the angle detector deviates from the practical direction of the ultrasonic beam due to a play involved in the torsional direction of the coil wire, and as a result, a desirous image can not precisely be displayed on a cathode ray tube. In addition, it is extremely difficult to correct such deviation.

In order to solve such a problem, it has heretofore been proposed to rotate the driving means such as a motor or the like at a constant speed, maintain a constant amount of deviation between the direction of the ultrasonic beam and the direction detected by the angle detector and correct the amount of deviation beforehand at the angle detector side.

But, if the distal end portion of the insertable portion is flexible as in the case of a flexible endoscope, the amount of deviation produced due to the play involved in the torsional direction cf the coil wire changes in accordance with the inclined angle of the distal end portion of the insertable portion. As a result, it is not proper to use as the angle detector a sin, cos function generation type potentiometer operative to detect an absolute value of the angle.

In an ultrasonic diagnosis apparatus inclusive of a coeliac cavity ultrasonic diagnosis apparatus and operative to effect a sector scan or radial scan of an ultrasonic beam for the purpose of displaying an ultrasonic image on a cathode ray tube, if use is made of a sin, cos function generation type potentiometer as an angle detection means of the ultrasonic beam, emission of ultrasonic pulses and scanning on the cathode ray tube are effected by a selfscanning system and the ultrasonic beam is scanned automatically or manually.

In the case of automatically scanning the ultrasonic beam, the driving means such as a motor or the like causes the ultrasonic beam to rotate at a constant speed, so that a deflecting angle of the ultrasonic beam may easily be synchronized with the space between successive emissions of the ultrasonic beam. As a result, it is possible to make the density of the scanning lines on the cathode ray tube constant. But, in the case of manually scanning the ultrasonic beam, it is almost impossible to synchronize the deflecting angle of the ultrasonic beam with the space between successive emissions of the ultrasonic beam, and hence to linearly change the deflecting angle for the cathode ray tube. Thus, the density of the scanning lines on the cathode ray tube is not constant, producing blurs.

In addition, in the above mentioned coeliac cavity ultrasonic diagnosis apparatus which can obtain the sector scan image, it has been proposed to rotate an ultrasonic oscillator per se as the ultrasonic beam scanning means. In this case, however, when the ultrasonic oscillator per se is rotated, its lead wire is twisted and it tends to be easily damaged. Particularly, when the ultrasonic oscillator is surrounded by an ultrasonic wave transmission medium such as water or the like, there is also a risk of the lead wire thus damaged being shortcircuited through water.

SUMMARY OF THE INVENTION

An object of the invention, therefore, is to provide a coeliac cavity diagnosis apparatus which can eliminate the above mentioned drawbacks which have been encountered with the prior art techniques and which can display on a cathode ray tube an ultrasonic image having an excellent picture quality without producing any angular deviation between the direction of the ultrasonic beam and the ultrasonic image.

A feature of the invention is the provision of an ultrasonic diagnosis apparatus including scanner portion insertable into a physical body of a patient and operative to effect a B-mode sector scan of an ultrasonic wave to produce a tomographic image, comprising (a) an endoscope including at least an observation means and illumination means and provided at its side surface near the distal end portion thereof with an opening;

(b) an ultrasonic signal transducer fixed to the distal end portion of the endoscope for generating and transmitting ultrasonic wave radiation is in a direction substantially aligned with the axial direction of an insertable portion of said endoscope;

(c) a reflecting mirror opposed to and inclined at substantially a constant angle with respect to the ultrasonic wave radiation surface of the ultrasonic signal transducer and rotatably mounted at the opening provided at the distal end portion of said endoscope;

(d) a power means provided in an operating portion located in the rear of said endoscope and operative to rotate said reflecting mirror;

(e) a flexible shaft extending through a flexible portion of said endoscope and transmitting the rotation of said power means to said reflecting mirror;

(f) an initial pulse generating means rotatable together with said reflecting mirror at the distal end portion of said endoscope to generate a pulse one time prior to the arrival of said reflecting mirror at a given position so as to define a display starting point at every ultrasonic scanning frame;

(g) an angle detecting means arranged in an operating portion located in the rear of said endoscope and rotatable in synchronism with a rotary shaft of said power means to detect the rotary angle of said power means and generate a pulse at every constant angle;

(h) means for obtaining a deflecting signal for reproducing an ultrasonic image from a pulse delivered from said initial pulse generating means and from a pulse delivered from said angle detecting means;

(i) a brightness modulating means operative to transmit the ultrasonic wave to said ultrasonic signal transducer and receive the ultrasonic wave therefrom to effect brightness modulation of the signal received; and (j) means for displaying the ultrasonic image from said deflecting signal and brightness modulating signal.

Further objects and features of the invention will be fully understood from the following detailed description with reference to the accompanying drawings, wherein:

BRIEF DESCRIPTION OF THE DRAWINGS

FIGS. 6, 7, 8 and 9 are block diagrams of various embodiments of a signal treating circuit shown in FIG. 1;

FIG. 10A is a side view of a further embodiment of means for generating a rotary angle analog signal;

FIG. 10B is a front view of a still further embodiment of means for generating a rotary angle analog signal;

FIG. 11 is a perspective view of one embodiment of means for generating a rotary angle digital signal;

FIG. 12 is a block diagram of a signal treating circuit operative to treat a rotary angle digital signal so as to display an ultrasonic image on a cathode ray tube;

FIGS. 13A and 13B are diagrammatic cross-sectional views of two embodiments of means for obtaining a start pulse to be supplied to a delay circuit shown in FIG. 12;

FIG. 14 is a block diagram of a circuit for obtaining a start pulse described with reference to FIG. 13A;

FIGS. 15A, 15B and 15C are signal wave diagrams for illustrating the operation of the circuit shown in FIG. 14; and FIGS. 16A and 16B are signal wave diagrams for illustrating the operation of obtaining the start pulse described with reference to FIG. 13B.

DETAILED DESCRIPTION OF PREFERRED EMBODIMENTS

Figure 1:
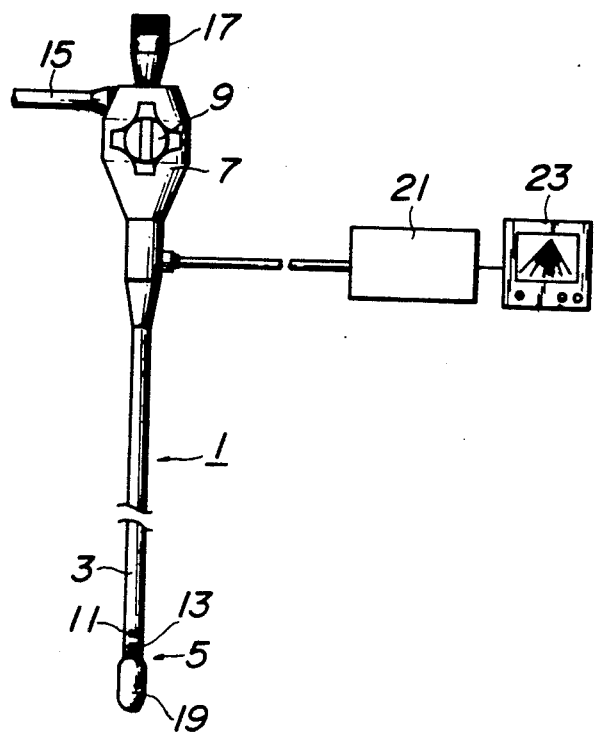
FIG. 1 is a front view of one embodiment of a coeliac cavity ultrasonic diagnosis apparatus according to the invention.

FIG. 1 shows one embodiment of a coeliac cavity ultrasonic diagnosis apparatus according to the invention which is mounted on a lateral view type endoscope and operative to display on a cathode ray tube a desirous organ in a coeliac cavity for the purpose of diagnosis.

An endoscope 1 includes a flexible insertable portion 3 a distal end portion 5 of which is made freely bendable toward any desired direction when an operating handle 9 provided at an endoscope operating portion 7 is rotated. The distal end portion 5 is provided with an observation window 11 and illumination window 13 located adjacent with each other. The illumination window 13 is optically connected to a light source (not shown) through a light guide to be described later and extending through the insertable portion 3, operating portion 7 and protective pipe 15 and operative to illuminate the inside of the coeliac cavity. The observation window 11 is optically connected to an observation portion 17 provided with an eyepiece through an image guide to be described later and extending through the insertable portion 3 and operating portion 7 and operative to observe the image in the coeliac cavity illuminated by the above mentioned illumination optical system.

In the present embodiment, the endoscope 1 is provided near that portion of the distal end portion thereof which is provided with the observation window 11 and illumination window 13 with an enclosing portion 19. In the enclosing portion 19 are enclosed an ultrasonic signal transducer, also called herein an ultrasonic oscillator which will be described later and which is made stationary and operative to transmit an ultrasonic beam therefrom and receive it and an ultrasonic reflecting mirror which is rotatably mounted and opposed to the ultrasonic oscillator.

In addition, near the ultrasonic reflecting mirror are arranged a rotary disc which is rotatable together with the ultrasonic reflecting mirror and a rotary angle detection means operative to detect the rotary angle of the rotary disc to detect the scanning position of the ultrasonic beam.

In the operating portion 7 is arranged a driving means for rotating the ultrasonic wave reflecting mirror together with the rotary disc. The driving means is connected to the ultrasonic reflecting mirror and rotary disc through a flexible power transmission member extending through the insertable portion 3.

In addition, the endoscope 1 is provided at its outside with a signal treating circuit 21 operative to control the transmission and reception of the ultrasonic beam delivered from the ultrasonic oscillator mounted on the endoscope 1 and control the rotation of the driving means and also operative to treat the signal received by the ultrasonic oscillator and treat the angular information delivered from the rotary angle detecting means. The signal treating circuit 21 is connected to a cathode ray tube 23 of a monitor device to reproduce an ultrasonic image.

Figure 2:
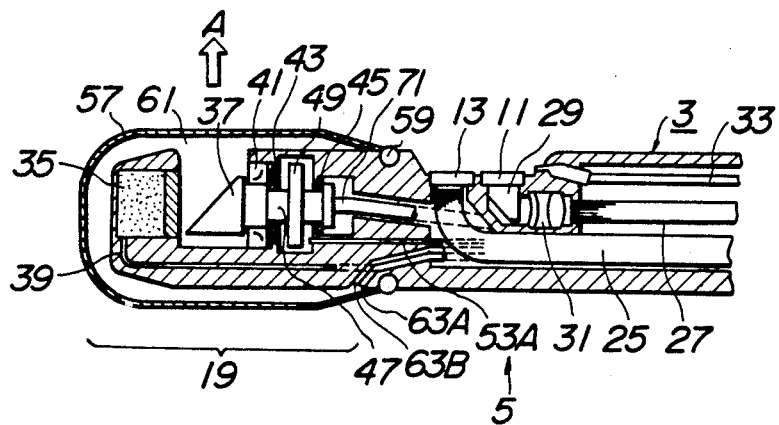
FIG. 2 is a detailed cross-sectional view of one embodiment of an insertable distal end portion shown in FIG. 1.
Figure 3:
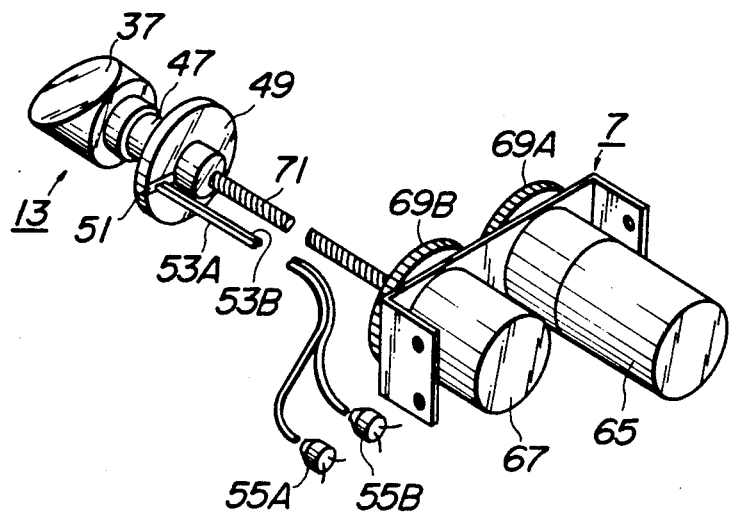
FIG. 3 is a perspective view of an ultrasonic reflecting mirror, rotary disc, rotary angle detecting means, driving means and power transmission member described with reference to FIG. 2.

FIG. 2 shows in detail one embodiment of a distal end portion of the insertable portion of the coeliac cavity ultrasonic diagnosis apparatus according to the invention shown in FIG. 1 and FIG. 3 shows in detail the ultrasonic reflecting mirror, rotary disc, rotary angle detecting means, driving means and power transmission member. Through the flexible insertable portion 3 are extended a light guide 25 for guiding an illumination light and an image guide 27 for transmitting an image of a coeliac cavity of a physical body. Light emission end of the light guide 25 is opposed to the illumination window 13 composed of a glass fitted to the insertable portion 3 so as to illuminate the inside of the coeliac cavity. The image in the coeliac cavity thus illuminated can be observed by the naked eye from the observation portion 17 through the observation window 11 composed of a glass, prism 29, image forming optical system 31 and image guide 27. The surfaces of the observation and illumination windows 11, 13 may be washed and cleaned by water or the like supplied through a water supply pipe 33 extending through the insertable portion 3.

The insertable portion 3 is provided at its distal end portion with an enclosing portion 19 which encloses therein an ultrasonic oscillator 35 made stationary and for transmitting an ultrasonic beam therefrom and receiving it and an ultrasonic reflecting mirror 37 rotatably mounted and opposed to the ultrasonic oscillator 35. Input and output signals of the ultrasonic oscillator 35 are received from and supplied into the signal treating circuit 21 through a signal cable 39 extending through the insertable portion 3. That surface of the ultrasonic reflecting mirror 37 which is opposed to the ultrasonic oscillator 35 is inclined at 45° to the vertical surface of the ultrasonic oscillator 35 so as to effect the sector scan of the ultrasonic beam emitted from the ultrasonic oscillator 35 toward a direction which is substantially perpendicular to the lengthwise direction of the insertable portion 3 as shown by an arrow A in FIG. 2. The echo reflected is made incident through the ultrasonic reflecting mirror 37 on the ultrasonic oscillator 35. The ultrasonic reflecting mirror 37 is secured to a shaft 47 rotatably supported by a sealing material 41 and bearings 43, 45. The shaft 47 is provided with a rotary disc 49 made integral therewith and operative to detect the rotary angle of the ultrasonic reflecting mirror 37, that is, the sector scan position of the ultrasonic beam.

In the present embodiment, the rotary disc 49 is provided at one of surfaces thereof with a strip-shaped reflecting portion 51 extending in a radial direction of the rotary disc 49 as shown in FIG. 3. To that surface side of the rotary disc 49 which is provided with the reflecting portion 51 are opposed respective ends of a pair of optical fibers 53A, 53B, the other ends of these optical fibers being extended through the insertable portion 3 and opposed to a light emitting element 55A and light receiving element 55B provided in the endoscope operating portion 7. The enclosing portion 19 is covered with a balloon 57 formed of rubber, organic resin or the like. The opening portion of the balloon 57 is hermetically sealed to the distal end portion 5 of the insertable portion 3 by means of an O-ring 59, for example. The insertable portion 3 is provided therein with water supply and discharge pipes 63A, 63B communicating with the interior portion 61 of the balloon 57 and adapted to selectively supply an ultrasonic wave transmission medium such as water or the like to the interior portion 61 of the balloon 57.

Meanwhile, the endoscope operating portion 7 is provided therein not only with the above mentioned light emitting element 55A and light receiving element 55B, but also with a motor 65 and an angle detector 67 such as a rotary encoder or a potentiometer which is operative to generate a pulse every time the motor 65 is rotated for a given angle as shown in FIG. 3. The rotation of the motor 65 is transmitted through gears 69A, 69B to the angle detector 67. In addition, the angle detector 67 is connected through a flexible power transmission member 71 such as a coil wire or the like extending through the insertable portion 3 to the ultrasonic reflecting mirror 37 which is rotated from the motor 65 through the gears 69A, 69B and power transmission member 71.

In the apparatus constructed as above described, the light emitted from the light emitting element 55A is incident through an optical fiber 53A on one of the surfaces of the rotary disc 49. As the ultrasonic reflecting mirror 37 and rotary disc 49 as a whole are rotated from the motor 65 through the gears 69A, 69B and power transmission member 71, a strong reflecting light is incident on the light receiving element 55B only when the reflecting portion 51 formed on one of the surfaces of the rotary disc 49 comes into a position opposed to the optical fibers 53A, 53B, and as a result, it is possible to deliver from the light receiving element 55B a scan starting signal representing the sector scan starting position of the ultrasonic beam, that is, the absolute rotary angle of the rotary disc 49 as its output.

Meanwhile, between the ultrasonic reflecting mirror 37 and the angle detector 67 driven from the motor 65 through the power transmission member 71, there occurs a deviation due to a play involved in the torsional direction of the power transmission member 71 when compared with the standstill condition thereof. The amount of deviation is changed in response to the load condition of the power transmission member 71 due to the rotary speed of the motor 65, degree of bending of the insertable portion 3 and friction at various portions. Let it be assumed that irregular amount of deviation produced during one revolution of the motor 65 be disregarded, if a relative rotary angle started from the scan starting signal delivered from the light receiving element 55B and detected by the angle detector 67 is measured, it is possible to obtain a true angular information showing the absolute direction of the ultrasonic beam. Such measure is extremely effective as a means for detecting the absolute direction of the ultrasonic beam in a coeliac cavity ultrasonic diagnosis apparatus including a flexible insertable portion whose degree of bending is suitably changed in use.

Figure 4:
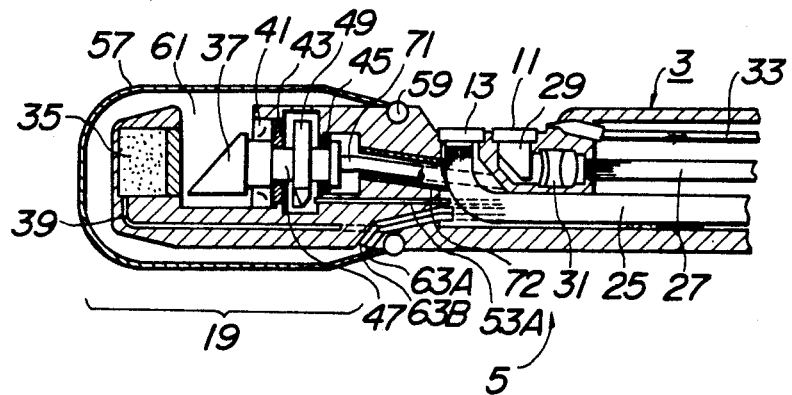
FIG. 4 is a detailed cross-sectional view of another embodiment of an insertable distal end portion shown in FIG. 1.
Figure 5:
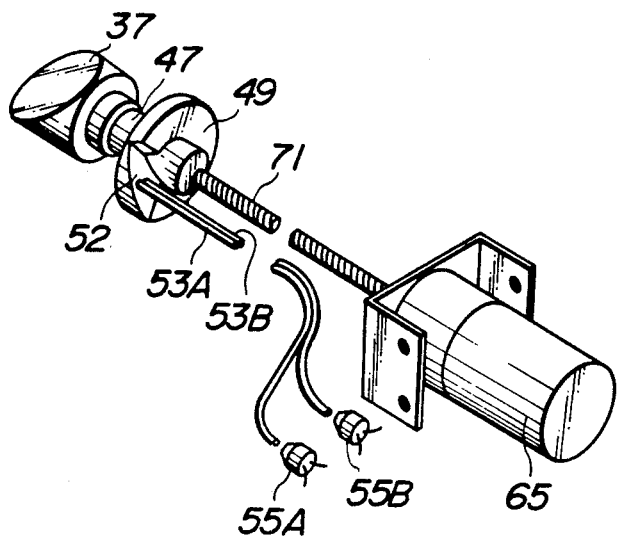
FIG. 5 is a perspective view of an ultrasonic reflecting mirror, another embodiment of a rotary disc, rotary angle detecting means, driving means and power transmission member described with reference to FIG. 4.

FIG. 4 shows in detail another embodiment of the distal end portion of the insertable portion of the coeliac cavity ultrasonic diagnosis apparatus according to the invention shown in FIG. 1 and FIG. 5 shows in detail the ultrasonic reflecting mirror, another embodiment of the rotary disc shown in FIGS. 2 and 3, and the rotary angle detecting means and power transmission member.

In the present embodiment, the rotary disc 49 is provided at one of surfaces thereof with a tapering inclination 52 which corresponds to a sector scan range (about 90 degrees) of the ultrasonic beam and which is treated to effect total reflection. To the tapering inclination 52 are opposed ends of a pair of optical fibers 53A, 53B the other ends of which are extended through the insertable portion 3 and opposed to the light emitting element 55A and light receiving element 55B provided in the endoscope operating portion 7.

When the power transmission member 71 is bent or rotated, it tends to be brought into contact with and to damage the light guide 25, image guide 27 or the like. In the present embodiment, in order to prevent such damage of the light guide 25, image guide 27 or the like, the power transmission member 71 is extended through a flexible pipe 72 composed of a teflon tube, for example.

The light emitted from the light emitting element 55A is incident through the optical fiber 53A on the tapering inclination 52 of the rotary disc 49 and reflected. The light thus reflected is incident through the optical fiber 53B on the light receiving element 53B. Since the tapering inclination 52 is tapered in configuration, when the rotary disc 49 and hence the ultrasonic reflecting mirror 37 is rotated, the distance between the light emitting end surface of the optical fiber 53A and light incident end surface of the optical fiber 53B on the one hand and the tapering inclination 52 on the other hand is continuously changed to correspondingly change the amount of light incident on the light receiving element 55B. As a result, it is possible to obtain from the output delivered from the light receiving element 55B angular information representing the rotary angle of the rotary disc 49 and hence of the ultrasonic reflecting mirror 37.

If the output delivered from the light receiving element 55B is a non-linear one, it is possible to easily correct such output to a linear one by means of a proper correction circuit. If it is desired to obtain digital angular information, the analog angular information detected as above described may be converted into a digital value by means of an analog-to-digital converter.

Figure 6:
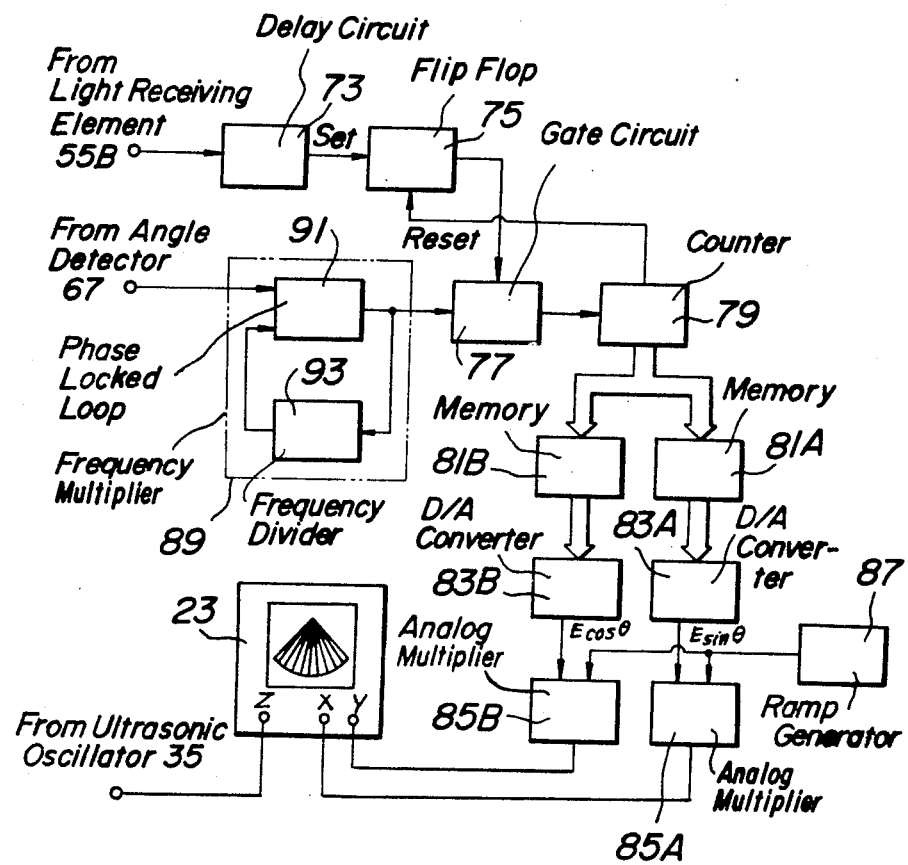

FIG. 6 shows one embodiment of a signal treating circuit 21 shown in FIG. 1.

The scan starting signal delivered from the light receiving element 55B shown in FIG. 3 is supplied to a delay circuit 73 and delayed by a given time and then supplied to a flipflop 75 so as to set it. The flipflop 75 causes a gate circuit 77 to open. The delay circuit 73 also functions to effect a minute adjustment for bringing the direction of the scanning line displayed on the cathode ray tube 23 of the monitor device into agreement with the true direction of the ultrasonic beam.

Meanwhile, the pulse delivered from the angle detector 67 such as a rotary encoder is supplied through a gate circuit 77 to a counter 79. The counter 79 functions to determine a sector angle to be displayed on the cathode ray tube 23 by a value set to the counter 79. If the counter 79 is operative to count pulses up to the set value thereof, the counter 79 causes the flipflop 75 to reset, thereby closing the gate circuit 77. Successive count values of the counter 79 are supplied to nonvolatile memories 81A, 81B, respectively, so as to specify addresses thereof. The nonvolatile memories 81A, 81B store digital values corresponding to sin $\theta$ and cos $\theta$ dependent on the deflecting angle $\theta$ of the ultrasonic beam and deliver as an output a functional value of the addresses specified by the output from the counter 79. The output from the nonvolatile memories 81A, 81B are supplied to D/A converters 83A, 83B, respectively, and converted into analog voltage values E sin $\theta$ and E cos $\theta$, respectively, and then supplied to analog multipliers 85A, 85B, respectively. The outputs delivered from the D/A converters 83A, 83B are not continuously changed in voltage, but are just the same as the outputs delivered from sin $\theta$, cos $\theta$ function generator type potentiometers which have heretofore been used as the angle detector. To the analog multipliers 85A, 85B are supplied sawtooth waves from a sawtooth wave generator, that is, a ramp generator 87. In the analog multipliers 85A, 85B, the sawtooth waves are multiplied by the outputs delivered from the D/A converters 83A, 83B to produce deflecting signals for the cathode ray tube 23. These deflecting signals are supplied to X and Y axis terminals of the cathode ray tube 23, respectively. To a Z axis terminal of the cathode ray tube 23 is supplied an output delivered from the ultrasonic oscillator 35 and subjected to amplification and detection so as to effect brightness modulation, thereby displaying an ultrasonic tomographic image on the cathode ray tube 23.

If the angle detector 67 is deficient in its angle resolving power, the output delivered from the angle detector 57 is supplied through a frequency multiplier 89 shown by dot-dash lines in FIG. 6 to the gate circuit 77. The frequency multiplier 89 is composed of a phase locked loop 91 supplied with pulses delivered from the angle detector 67 and a frequency divider 93 operative to divide the frequency of the output from the phase locked loop 91 into I/N and supply the output thereof to a phase detection input terminal of the phase locked loop 91. The use of such measure ensures an increase of the angle resolving power to a value which is substantially N times larger than the angle resolving power of the angle detector 67 itself and provides the important advantage that it is possible to obtain a picture image having a higher scanning line density.

FIG. 7 shows another embodiment of the signal treating circuit 21 shown in FIG. 1.

In the present embodiment, the voltage proportional to the deflecting angle of the ultrasonic beam delivered from the angle detector 67 such as a rotary encoder shown in FIG. 3 is supplied through an A/D converter 78 to the counter 79. In the counter 79, the total digital output delivered from the A/D converter 78 corresponds to the absolute value of the analog output voltage delivered from the angle detector 67, but the least significant bit output delivered from the A/D converter 78 is changed when the deflecting angle of the ultrasonic beam is changed by a constant angle. As a result, if use is made of the least significant bit output only delivered from the A/D converter 78, it is possible to obtain the pulse corresponding to the angular change only of the ultrasonic beam independently of the amount of deviation of the angle detector 67 from the practical direction of the ultrasonic beam. Then, the pulse thus obtained is counted by the counter 79 as described above with reference to FIG. 6.

FIG. 8 shows a further embodiment of the signal treating circuit 21 shown in FIG. 1.

In the present embodiment, the motor 65 is energized from an electric source 95 to rotate at a constant speed. As above described, the rotation of the motor 65 is transmitted through the power transmission element 71 to the rotary disc 49 and ultrasonic reflecting mirror 37, so as to rotate the rotary disc 49 like in FIG. 5 and ultrasonic reflecting mirror 37 at a constant speed. The rotation angle of the ultrasonic mirror 37 is detected by the absolute angle detecting device 200 like that shown in FIG. 5. The signal thus generated is supplied to a sin $\theta$ generator 97 and cos $\theta$ generator 99 to generate a sin $\theta$ signal and cos $\theta$ signal, respectively.

The output delivered from the absolute angle detecting device 200 is also supplied to a comparative circuit 101 of an ultrasonic wave transmitting and receiving signal treating circuit 103 including the ultrasonic oscillator 35 so as to generator a pulse everytime the rotary disc 49 and hence the ultrasonic reflecting mirror 37 is rotated by a given angle $\theta_0$. The pulse thus generated is supplied to a trigger pulse generator 105 to generate a trigger pulse. The trigger pulse is supplied to a sawtooth wave generator 107 to generate a sawtooth wave of At (when A is a constant and t is the lapse of time from generation of the ultrasonic pulse). This sawtooth wave and the above mentioned sin $\theta$ and cos $\theta$ signals are supplied to a sweep signal generator 109 composed of a multiplier to generate a sawtooth wave like deflecting signal and blanking signal for the cathode ray tube 23 of the monitor device. These deflecting and blanking signals are supplied through an amplifier 111 to X axis and Y axis terminals of the cathode ray tube 23, respectively.

The trigger pulse delivered from the trigger pulse generator 105 is also supplied to a high frequency pulse generator 113 to generate a high frequency pulse. This high frequency pulse is supplied to a power amplifier 115 and amplified by it and then supplied through a switching circuit 117 to the ultrasonic oscillator 35. In this way, the scan of the ultrasonic reflecting mirror 37 becomes synchronized with the sweep in the cathode ray tube 23.

The ultrasonic wave radiated from the ultrasonic oscillator 35 is reflected by the physical body and returned to the ultrasonic oscillator 35 again in which the ultrasonic wave is converted into an electric signal. This signal is supplied through the switching circuit 117 to an RF amplifier 119 and amplified by it. The signal thus amplified is supplied to a detector circuit 121 and detected by it. The signal thus detected is supplied to an amplifier 123 and amplified by it and then is supplied to a Z axis terminal of the cathode ray tube 23 as its brightness modulating signal. The switching circuit 117 functions to protect the RF amplifier 119 from being subjected to a difference between the driving electric power of the ultrasonic oscillator 35 and the electric power produced from the ultrasonic wave reflected from the physical body. In this way, it is possible to display the sector scan image by polar coordinates on the screen surface of the cathode ray tube 23.

FIG. 9 shows a still further embodiment of the signal treating circuit 21 shown in FIG. 1.

In the present embodiment, the analog rotary angular signal delivered from the angle detector 67 including the light receiving element 55B is supplied to an amplifier 125 and amplified by it and then supplied to an A/D converter 127 and converted into a digital value. The digital value thus obtained is applied to read only memories 129, 131 to specify their addresses. The read only memories 129, 131 have stored therein digital values corresponding to sin $\theta$ and cos $\theta$ dependent on the deflecting angle $\theta$ of the ultrasonic reflecting mirror 37, that is, the ultrasonic beam and deliver as outputs the function values of the addresses specified by the output delivered from the A/D converter 127. The digital values representing the above mentioned function values are supplied to D/A converters 133, 135 to convert the digital values to analog voltage values E sin $\theta$ and E cos $\theta$ and then supplied to analog multipliers 137, 139, respectively. Meanwhile, the least significant bit signal, for example, of the output delivered from the A/D converter 127 is supplied to a ramp generator 141 to generate a sawtooth wave therefrom. This sawtooth wave is supplied to analog multipliers 137, 139 which function to multiply the sawtooth wave by the outputs delivered from the D/A converters 133, 135 to produce deflecting signals. These deflecting signals are supplied to X axis and Y axis terminals of the cathode ray tube 23 of the monitor device, respectively. The least significant one bit output signal delivered from the A/D converter 127 is supplied to the trigger pulse generator 105 or to the high frequency pulse generator 113 of the ultrasonic wave transmitting and receiving signal treating circuit 103 shown in FIG. 8 to effect the signal treatment in the same manner as described above to obtain a brightness modulating signal. The brightness modulating signal thus obtained is supplied to the Z axis terminal of the cathode ray tube 23 of the monitor device to display the sector scan image of the ultrasonic beam on the cathode ray tube 23 in polar coordinates.

In the embodiment shown in FIG. 5, the rotary disc 49 is provided with the tapering inclination 52 so as to detect the change of the amount of light due to the change of the light passage and to obtain the rotary angle analog signal.

Alternatively, to the rotary disc 49 provided with the same tapering inclination 52 may be opposed an eddy current detector 143 as shown in FIG. 10A to detect the distance between the tapering inclination 52 and the eddy current detector 143 so as to obtain the rotary angle analog signal in the same manner as in the case shown in FIG. 5.

FIG. 10B shows a further embodiment of the rotary disc 49 shown in FIG. 5. In the present embodiment, that portion 145 of the rotary disc 49 which corresponds to the sector scan range of the ultrasonic beam is magnetized in a manner such that the strength of magnetization is continuously changed in the rotary direction of the rotary disc 49 and this strength of magnetization is detected by a magnetic sensor to obtain a rotary angle analog signal which is the same as that obtained in the above described manner.

In addition, in the rotary disc 49 shown in FIG. 10B, the light reflection rate in the above mentioned portion 145 may be continuously changed to obtain a rotary angle analog signal from the strength of the reflected light in the same manner as that described above.

Alternatively, the light transmission rate of the above mentioned portion 145 may be continuously changed and to this portion 145 may be opposed the light emitting and receiving elements to obtain the same rotary angle analog signal from the amount of light incident on the light receiving element.

Various means for obtaining the analog rotary angular signal representing the deflecting angle of the ultrasonic beam from the rotary disc rotatable together with the ultrasonic reflecting mirror may be conceived. Such means is based on the fact that when use is made of the rotary disc including the tapering inclination the change in distance from the reference position to a raised portion of the tapering inclination is detected to obtain the analog rotary angle signal and that when use is made of the flat-shaped rotary disc the information density is continuously changed in the rotary direction so as to detect the desired information by the sensor to obtain the analog rotary angle signal.

As stated hereinbefore, it is possible to obtain the analog rotary angle signal from the rotary disc rotatable together with the ultrasonic reflecting mirror.

Alternatively, information representing the rotary angle may be digitally recorded on a desired portion of the rotary disc and this digital information may be read out to obtain a digital rotary angle signal (a pulse signal).

FIG. 11 shows a rotary disc 49 which is provided at that portion thereof which corresponds to the sector scan range thereof with a number of slits 147 representing the rotary angle and extending in a radial direction and to both surfaces of which are opposed the light emitting element 55A and the light receiving element 55B, respectively, such that the light passed through the slit 147 is received by the light receiving element 55B to obtain a desired digital signal. In the present embodiment, the light flux passed through the slit 147 may suitably by concentrated by means of a lens or fiber.

The slits 147 formed on the rotary disc 49 may be replaced by a reflecting surface which is operative to receive the reflected light in the above described manner to obtain a desired digital signal. Alternatively, that portion of the rotary disc 49 which is provided with the slits 147 may be magnetized and the strength of magnetization may be magnetically detected to obtain a desired digital signal.

FIG. 12 shows another embodiment of the signal treating circuit 21 shown in FIG. 1 which can suitably treat the digital angle signal (the pulse signal) to display the sector scan image on the cathode ray tube 23 of the monitor device.

In the present embodiment, a start pulse representing sector scan start is supplied to a delay circuit 149 to delay the pulse by a given time. Then, the pulse is supplied to a flipflop 151 to set it, thereby opening a gate circuit 153.

The delay circuit 149 functions to effect minute adjustment for bringing the direction of the scanning lines displayed on the cathode ray tube 23 into agreement with the true directions of the ultrasonic beam.

An angle detection pulse representing the rotary angle is supplied through the gate circuit 153 to a counter 155. The counter 155 functions to determine the sector angle to be displayed by the set value thereof. If the counter 155 counts the number of pulses up to the set value thereof, the counter 155 causes the flipflop 151 to clear, thereby closing the gate circuit 153. Successive count values of the counter 155 are supplied to nonvolatile read only memories 157, 159, respectively, so as to specify addresses thereof. The read only memories 157, 159 function to store digital values corresponding to sin $\theta$ and cos $\theta$ dependent on the deflecting angle $\theta$ of the ultrasonic beam and to deliver as outputs the function values of the addresses specified by the output delivered from the counter 155. The outputs delivered from the read only memories 157, 159 are supplied to D/A converters 161, 163 and converted into analog voltage values E sin $\theta$ and E cos $\theta$, respectively, which are then supplied to analog multipliers 165, 167 respectively. The outputs delivered from the D/A converters 161, 163 are not continuously changed in voltage, but are just the same as the outputs delivered from sin $\theta$ and cos $\theta$ generator type potentiometers which have heretofore been used as the angle detector.

In the present embodiment, the angle detector pulse delivered from the gate circuit 153 is also supplied to a ramp generator 169 which is operative to generate a sawtooth wave. The sawtooth wave is supplied to the analog multipliers 165, 167, respectively, which are operative to multiply the sawtooth wave by the outputs delivered from the D/A converters 161, 163 to produce deflecting signals for the cathode ray tube 23. These deflecting signals are supplied to X axis and Y axis terminals of the cathode ray tube 23, respectively.

The angle detection pulse delivered from the gate circuit 153 is also supplied to the high frequency pulse generator 113 of the ultrasonic transmitting and receiving signal treating circuit 103 shown in FIG. 8 to effect the above mentioned treatment which is the same as the above described treatment so as to obtain a brightness modulation signal which is then supplied to the Z axis terminal of the cathode ray tube 23, thereby displaying the sector scan image of the ultrasonic beam in polar coordinates. If angle detection pulse is deficient in the angle resolving power, the angle detection pulse is supplied through a frequency multiplier 171 shown by dot-dash lines in FIG. 12 to the gate circuit 153. The frequency multiplier 171 is composed of a phase locked loop 173 and a frequency divider 175 operative to divide the frequency of the output delivered from the phase locked loop 173 by N and to supply the output having 1/N frequency to the phase detection input terminal of the phase locked loop 173, thereby effecting the frequency multiplication. In this way, the angle resolving power becomes substantially N times larger, and as a result, it is possible to obtain a picture image having a higher scanning line density.

The signal treating circuit shown in FIG. 12 uses a start pulse for the sector scan. This start pulse may be obtained from a sensor which is the same as that used to obtain the angle detection pulse by making the reflection rate, transmission rate or the strength of magnetization of that portion of the rotary disc which corresponds to the start pulse different from that of the other portion representing the rotary angle.

For example, the slits 147 shown in FIG. 11 and delivering the start pulse are made longer in the radial direction and the start pulse thus delivered is detected by a separate sensor exclusively used for such detection to obtain the start pulse.

FIG. 13A shows another embodiment of means for obtaining a start pulse in which provision is made of a group of strips equally spaced apart from each other and delivering an angle detection pulse and a strip 177 located at a portion corresponding to the start position is made wide in width.

FIG. 13B shows a further embodiment of means for obtaining a start pulse in which provision is made of a group of strips equally spaced apart from each other and delivering an angle detection pulse, strips located at a portion corresponding to the start position being removed.

That is, in the embodiment shown in FIG. 13A, the output delivered from a strip detection sensor (not shown) is supplied to a monostable multivibrator 179 and a delay circuit 181 and the output delivered from the delay circuit 181 and a $\overline{Q}$ output delivered from the monostable multivibrator 179 are supplied to an AND circuit 183.

The pulses obtained from the sensor (not shown) correspond in pitch and width with the strips as shown in FIG. 15A. The $\overline{Q}$ output pulses delivered from the monostable multivibrator 179 are shown in FIG. 15B. The output pulses delivered from the sensor and shown in FIG. 15A are somewhat delayed by the delay circuit 181, and as a result, it is possible to obtain a start pulse shown in FIG. 15C.

In the embodiment shown in FIG. 13B, the output pulses delivered from a strip detection sensor (not shown) become pulses shown in FIG. 16A. If the pulses shown in FIG. 16A are supplied to a retrigger monostable multivibrator, it is possible to obtain a start pulse shown in FIG. 16B from the output therefrom.

The invention is not limited to the above mentioned embodiments, but various changes and alternations may be made. For example, in the above mentioned embodiments, the ultrasonic oscillator 35 is made stationary and the ultrasonic reflecting mirror 37 is rotated so as to effect the sector scan of the ultrasonic beam. But, the ultrasonic oscillator 35 may directly be rotated so as to effect the sector scan of the ultrasonic beam.

In addition, in the above mentioned embodiments, the position for starting the sector scan of the ultrasonic beam, that is, the absolute angle thereof is optically detected. But, the absolute angle may be detected by closing a mechanical switch composed of a rotor and brush.

The invention may effectively be applied not only to the above mentioned coeliac cavity ultrasonic diagnosis apparatus including the flexible insertable portion, but also to ultrasonic diagnosis apparatus which includes a rigid insertable portion, or which includes an ultrasonic beam scan means and its driving means enclosed in the distal end portion of the insertable portion and directly connected with each other, or in which the ultrasonic beam is emitted from the surface of the physical body of a patient.

In addition, the angular information may be formed on the rear surface of the ultrasonic reflecting mirror. In this case, the ultrasonic reflecting mirror may be used as the rotary disc. In the above described embodiments, the ultrasonic diagnosis apparatus according to the invention is incorporated into the endoscope including the image guide. Alternatively, the ultrasonic diagnosis apparatus according to the invention may also be incorporated into the endoscope including a solid state camera device instead of the image guide. In this case, the optical image and the ultrasonic image in the coeliac cavity may separately or selectively be displayed on the cathode ray tube of the monitor device.

It is now always necessary to incorporate the coeliac cavity ultrasonic diagnosis apparatus according to the invention into the endoscope.

As stated hereinbefore, in the ultrasonic diagnosis apparatus which includes a flexible insertable portion, the scan driving means and the ultrasonic beam scan means are connected with each other through the flexible power transmission member, and the ultrasonic beam is rotated at a constant speed so as to display on the cathode ray tube the sector scan or radial scan ultrasonic image, the invention makes use of the angle detector for detecting the angular change only and scan starting position detector instead of using the conventional angle detector for detecting the absolute angle and hence is capable of displaying on the cathode ray tube the ultrasonic image corresponding to the true ultrasonic beam direction independently of the amount of deviation of the direction to be detected by the angle detector from the actual direction of the ultrasonic beam. If the scan driving means is connected through the rigid shaft to the ultrasonic beam scan means and the sector scan is effected by manually or by reciprocal rotations, the scanning speed of the ultrasonic beam is not constant. Even in such case, if the transmission pulse is triggered by the output pulse delivered from the angle detector, the invention is capable of displaying on the cathode ray tube minute scanning lines at constant intervals and hence displaying an ultrasonic image having constant scanning line density intervals. Similarly, the invention is capable of displaying such ultrasonic image by a coeliac cavity ultrasonic diagnosis apparatus which includes a flexible insertable portion and in which the ultrasonic beam scanning means is manually driven from the outside through a wire or the like or by an ultrasonic diagnosis apparatus in which the sector scan is effected by emitting an ultrasonic pulse from the surface of a physical body into a coeliac cavity.

In addition, in the coeliac cavity ultrasonic diagnosis apparatus according to the invention, the ultrasonic oscillator is made stationary and the ultrasonic reflecting mirror is rotated so as to effect the sector scan of the ultrasonic beam and the rotary angle of the rotary disc rotatable together with the ultrasonic reflecting mirror is detected so as to obtain the deflecting angle of the ultrasonic beam. As a result, the invention is capable of using the ultrasonic oscillator in a stable state for a long time without damaging the wiring thereof and while obtaining precise angular information and a cathode ray tube display of an accurate picture image.

What is claimed is:
1. A coeliac cavity ultrasonic diagnosis apparatus including a scanner portion insertable into a physical body of a patient and operative to effect a B-mode sector scan of an ultrasonic wave to produce a tomographic image, comprising
   (a) an endoscope including at least an observation means and illumination means and provided at its side surface near the distal end portion thereof with an opening;

(b) an ultrasonic signal transducer fixed to the distal end portion of the endoscope for generating and transmitting ultrasonic wave radiation in a direction substantially aligned with the axial direction of an insertable portion of said endoscope;

(c) a reflecting mirror opposed to and inclined at substantially a constant angle with respect to the ultrasonic wave radiation surface of the ultrasonic signal transducer and rotatably mounted at the opening provided at the distal end portion of said endoscope;

(d) a power means provided in an operating portion located in the rear of said endoscope and operative to rotate said reflecting mirror;

(e) a flexible shaft extending through a flexible portion of said endoscope and transmitting the rotation of said power means to said reflecting mirror;

(f) an initial pulse generating means rotatable together with said reflecting mirror at the distal end portion of said endoscope to generate a pulse just prior to the arrival of said reflecting mirror at a given position so as to define a display starting point at every ultrasonic scanning frame;

(g) an angle detecting means arranged in said operating portion located in the rear of said endoscope and rotatable in synchronism with said rotary shaft of said power means to detect the rotary angle of said power means and generate a pulse each time said rotary shaft rotates by a constant angle;

(h) means for obtaining a reflecting signal for reproducing an ultrasonic image from a pulse delivered from said initial pulse generating means and from a pulse delivered from said angle detecting means;

(i) a brightness modulating means operative to transmit the ultrasonic wave to said ultrasonic signal transducer and receive the ultrasonic wave therefrom to effect brightness modulation of the signal received; and (j) means for displaying the ultrasonic image from said deflecting signal and brightness modulating signal.

2. The apparatus according to claim 1, wherein said means for obtaining a deflecting signal comprises:

a counter operative to commence counting on the basis of the pulse delivered from said initial pulse generating means and to be triggered by the pulse delivered from said angle detecting means;

a nonvolatile memory having an address specified by said counter and operative to deliver as an output a functional value of the specified address from the functional values of $\sin \theta$ and $\cos \theta$ corresponding to the deflecting angle of the ultrasonic bean stored therein; and a deflecting signal generating circuit for generating a deflecting signal for a cathode ray tube for reproducing an ultrasonic signal having an amplitude value which is proportional to the output value from said non-volatile memory.

3. The apparatus according to claim 1 or 2, wherein said initial value generating means comprises (a) a disc rotatable together with said reflecting mirror and provided at its one portion with a light reflecting portion;

(b) a light emitter and a light receiver arranged in a scanning portion located in the rear of the endoscope; and (c) two optical fibers extending through the endoscope and having ends opposed to said disc and the other ends opposed to said light emitter and light receiver, respectively.

4. The apparatus according to claim 1, or 2, wherein said angle detecting means comprises an optical rotary encoder.

5. The apparatus according to claim 1 or 2, wherein said angle detecting means comprises (a) a linear potentiometer; and (b) an A/D converter for converting an analog output delivered from said linear potentiometer into a digital value.

6. The apparatus according to claim 1, wherein said ultrasonic signal transducer, reflecting mirror and initial pulse generating means are enclosed in a deformable bag filled with an ultrasonic wave transmitting medium.

7. The apparatus according to claim 6, wherein said deformable bag is supplied with said ultrasonic wave transmitting medium through a supply pipe, said ultrasonic wave transmitting medium being discharged from said deformable bag through an exhaust pipe.

8. A coeliac cavity ultrasonic diagnosis apparatus including a scanner portion insertable into a physical body of a patient and operative to effect a B-mode sector scan to produce a tomographic image, comprising (a) an endoscope including at least an observation means and illumination means and provided at its side surface near the distal end portion thereof with an opening;

(b) an ultrasonic signal transducer fixed to the distal end portion of the endoscope for transmitting ultrasonic wave radiation in a direction substantially aligned with the axial direction of an insertable portion of the endoscope;

(c) a reflecting mirror opposed to an inclined at substantially a constant angle with respect to the ultrasonic wave radiation surface of the ultrasonic signal transducer and rotatably mounted at the opening provided at the distal end portion of the endoscope;

(d) a power means provided in an operating portion located in the rear of the endoscope and operative to rotate the reflecting mirror;

(e) a flexible shaft extending through said flexible portion of said endoscope and transmitting the rotation of said power means to said reflecting mirror;

(f) an angle detecting means rotatable together with said reflecting mirror and delivering as an output an analog value corresponding to the rotary angle of said reflecting mirror;

(g) an A/D converter for converting the analog output delivered from said angle detecting means into a digital value;

(h) means for obtaining a deflecting signal for reproducing an ultrasonic image from the digital value delivered from said A/D converter;

(i) a brightness modulating means for transmitting an ultrasonic wave to said ultrasonic signal transducer and receiving said ultrasonic wave from said ultrasonic signal transducer to effect brightness modulation of the signal received; and (j) means for displaying an ultrasonic image on a cathode ray tube from said deflecting signal and brightness modulating signal.

9. The apparatus according to claim 8, wherein said means for obtaining a deflecting signal comprises a nonvolatile memory having an address specified by the output delivered from said A/D converter and operative to deliver as an output a functional value of the specified address from the functional values of sin $\theta$ and cos $\theta$ corresponding to the deflecting angle of the ultrasonic beam stored therein; and a deflecting signal generating circuit for generating a deflecting signal for a cathode ray tube for reproducing an ultrasonic image signal having an amplitude value which is proportional to the output value from said nonvolatile memory.

10. The apparatus according to claims 8 and 9, wherein said angle detecting means comprises
   (a) a flat-shaped rotary disc rotatable together with said reflecting mirror and recorded with an angular information whose record concentration is continuously changed; and
   (b) means for reading out said angular information.

11. The apparatus according to claims 8 and 9, wherein said angle detecting means comprises
   (a) a rotary disc rotatable together with said reflecting mirror and provided at at least one portion with a tapering inclination; and
   (b) means for reading out angle information from a change in distance from said rotary disc.

12. The apparatus according to claim 11, wherein said angle detecting means comprises
   (a) a rotary disc rotatable together with said reflecting mirror and provided at its one portion with a tapering inclination;
   (b) a light emitter and light receiver arranged in an operating portion located in the rear of an endoscope; and
   (c) two optical fibers extending through a flexible portion of an endoscope and having ends opposed to said rotary disc and the other ends opposed to light emitter and light receiver, respectively.

13. The apparatus according to claim 11, wherein said angular detecting means comprises
   (a) a rotary disc rotatable together with said reflecting mirror and provided at its one portion with a tapering inclination, said rotary disc being composed of a metal conductor; and
   (b) an eddy current detector opposed to said rotary disc.

14. The apparatus according to claim 11, wherein said angle detecting means comprises
   (a) a rotary disc rotatable together with said reflecting mirror and provided at its one portion with a tapering inclination, said rotary disc being composed of a magnetized magnetic body; and
   (b) a magnetic sensor opposed to said rotary disc.

15. A coeliac cavity ultrasonic diagnosis apparatus including a scanner portion insertable into a physical body of a patient and operative to effect a B-mode sector scan of an ultrasonic wave to produce a tomographic image, comprising
   (a) an endoscope including at least an observation means and illumination means and provided at its side surface near the distal end portion thereof with an opening;
   (b) an ultrasonic signal transducer fixed to the distal end portion of the endoscope for generating and transmitting ultrasonic wave radiation in a direction substantially aligned with the axial direction of an insertable portion of said endoscope;
   (c) a reflecting mirror opposed to and inclined at substantially a constant angle with respect to the ultrasonic wave radiation surface of the ultrasonic signal transducer and rotatably mounted at the opening provided at the distal end of said endoscope;
   (d) a power means provided in an operating portion located in the rear of said endoscope and operative to rotate said reflecting mirror;
   (e) a flexible shaft extending through a flexible portion of said endoscope and transmitting the rotation of the power means to said reflecting mirror;
   (f) an angle detecting means rotatable together with said reflecting mirror and generating equally spaced pulses each time said reflecting mirror is rotated by a constant angle except for one rotation of said reflecting mirror by said constant angle during each revolution thereof;
   (g) an initial pulse generator circuit for producing a pulse signal from a row of pulses delivered from said angle detecting means each time said reflecting mirror is rotated by one revolution;
   (h) means for obtaining a deflecting signal for reproducing an ultrasonic image from the pulse delivered from said initial pulse generator means and from the pulse delivered from said angle detecting means;
   (i) a brightness modulating means for transmitting an ultrasonic wave to said ultrasonic signal transducer and receiving said ultrasonic wave therefrom and effecting brightness modulation of the signal received; and
   (j) means for displaying on a cathode ray tube an ultrasonic image from said deflecting signal and said brightness modulation signal.

16. The apparatus according to claim 15, wherein said means for obtaining said deflecting signal comprises
   a counter for commencing counting on the basis of the pulse delivered from said initial pulse generating means and operative to be triggered by the pulse delivered from said angle detecting means;
   a nonvolatile memory having addresses specified by said counter and delivering as an output functional values of the specified addresses from the functional values of sin and cos corresponding to the deflecting angle of the ultrasonic beam stored therein; and
   a deflecting signal generator circuit for generating a deflecting signal for a cathode ray tube for reproducing an ultrasonic image signal having an amplitude value corresponding to the output value delivered from said nonvolatile memory.

17. The apparatus according to claims 15 or 16, wherein said angle detecting means comprises
   (a) a flat-shaped rotary disc rotatable together with said reflecting mirror; and
   (b) means for reading out an information recorded on said rotary disc.

18. The apparatus according to claim 17, wherein said angle detecting means comprises
   (a) a rotary disc rotatable together with said reflecting mirror and magnetically recorded with equally spaced signals along its periphery, said signals being removed from one peripheral portion of said rotary disc; and
   (b) a magnetic head opposed to said rotary disc.

19. The apparatus according to claim 17, wherein said angle detecting means comprises
   (a) a rotary disc rotatable together with said reflecting mirror and provided along its periphery with equally spaced apart gradings except at one peripheral portion thereof; and (b) light emitting and light receiving elements opposed to opposite side surfaces of said rotary disc, respectively.

20. The apparatus according to claim 17, wherein said angle detecting means comprises
   (a) a rotary disc rotatable together with said reflecting mirror and provided along its periphery except at one portion with equally spaced apart gradings;
   (b) a light emitter and light receiver arranged in a scannng portion located in the rear of said endoscope; and
   (c) two optical fibers extending through a flexible portion of said endoscope and having ends opposed to said rotary disc and the other ends opposed to said light emitter and light receiver, respectively.

21. The apparatus according to claims 15 or 16, wherein said start pulse generating means comprises
   (a) a rotary disc provided along its periphery except one portion with equally spaced apart recorded informations;
   (b) means for reading out said recorded informations; and
   (c) a retrigger monostable multivibrator supplied with said read out recorded informations to obtain a start pulse.

22. The apparatus according to claims 4 or 14, wherein said start pulse generating means comprises
   (a) a rotary disc provided along its periphery except one portion with equally spaced apart recorded information, said one portion being provided with a recorded information which is wide in width compared to other recorded information;
   (b) means for reading out said recorded information;
   (c) a monostable multivibrator and delay circuit connected in parallel and supplied with said read out recorded information; and
   (d) an AND circuit supplied with the output delivered from said monostable multivibrator and delay circuit.

* * * * *